(12) United States Patent
Tang et al.

(10) Patent No.: US 12,035,960 B2
(45) Date of Patent: Jul. 16, 2024

(54) DUAL-CHANNEL INJECTION BIPOLAR HIGH FREQUENCY ELECTROSURGICAL KNIFE

(71) Applicant: Micro-Tech (Nanjing) Co., Ltd., Nanjing (CN)

(72) Inventors: Zhi Tang, Nanjing (CN); Mingqiao Fan, Nanjing (CN); Huan Xie, Nanjing (CN); Changqing Li, Nanjing (CN); Derong Leng, Nanjing (CN)

(73) Assignee: Micro-Tech (Nanjing) Co., Ltd., Nanjing (CN)

( * ) Notice: Subject to any disclaimer, the term of this patent is extended or adjusted under 35 U.S.C. 154(b) by 1004 days.

(21) Appl. No.: 16/970,584

(22) PCT Filed: Sep. 7, 2018

(86) PCT No.: PCT/CN2018/104476
§ 371 (c)(1),
(2) Date: Aug. 17, 2020

(87) PCT Pub. No.: WO2019/169843
PCT Pub. Date: Sep. 12, 2019

(65) Prior Publication Data
US 2021/0113260 A1    Apr. 22, 2021

(30) Foreign Application Priority Data
Mar. 7, 2018  (CN) .......................... 201810184576.6

(51) Int. Cl.
*A61B 18/14*    (2006.01)
*A61M 5/14*    (2006.01)
(Continued)

(52) U.S. Cl.
CPC ........... *A61B 18/14* (2013.01); *A61M 5/1407* (2013.01); *A61M 5/19* (2013.01);
(Continued)

(58) Field of Classification Search
CPC ..... A61B 18/12; A61B 18/14; A61B 18/1492; A61B 18/148; A61B 2018/00601;
(Continued)

(56) References Cited

U.S. PATENT DOCUMENTS 4,682,596 A    7/1987  Bales et al.
5,403,311 A *  4/1995  Abele ................ A61B 18/1492
                                                        606/49

(Continued)

FOREIGN PATENT DOCUMENTS

CN          1868416 A    11/2006
CN         201987658 U     9/2011
(Continued)

OTHER PUBLICATIONS

International Search Report dated Nov. 13, 2018, for corresponding International Patent Application No. PCT/CN2018/104476, filed Sep. 7, 2018.

(Continued)

*Primary Examiner* — Thomas A Giuliani
(74) *Attorney, Agent, or Firm* — Mai D. Lauer; Westman, Champlin & Koehler P.A.

(57) ABSTRACT

Dual-channel injection bipolar high frequency electrosurgical knife comprises an electrode part, a main part and an operation part. The electrode part comprises an active electrode, an insulating part and an inert electrode. The active electrode has a hollow tubular portion, which can cut the target lesion tissue when power on. The main part comprises a protective tube, an insulation sheath and an insulation coated screw, connector, seal. The insulation coated screw includes a conductive screw and an insulating coating on the surface. The operation part comprises a positioning structure, a slider, a core rod, a connection sheath, an infusion tube and a connection cable. 6% Luer tapers are attached to (Continued)

both the positioning structure and the infusion tube. Liquid can flow out from the dual-channel, a solution can be injected in submucosal layer to elevate the mucous membrane tissue or clean hemorrhage site.

20 Claims, 8 Drawing Sheets

(51) Int. Cl.
  *A61M 5/19*  (2006.01)
  *A61B 18/00*  (2006.01)
  *A61B 18/12*  (2006.01)

(52) U.S. Cl.
  CPC .............. *A61B 2018/00083* (2013.01); *A61B 2018/00148* (2013.01); *A61B 2018/00601* (2013.01); *A61B 2018/126* (2013.01); *A61B 2018/1412* (2013.01); *A61B 2018/1475* (2013.01)

(58) Field of Classification Search
  CPC ...... A61B 2018/126; A61B 2018/1412; A61B 2018/1475; A61B 2018/00982; A61B 2018/1417; A61B 2018/162; A61B 2018/00577; A61B 2018/00607; A61B 2018/1472; A61B 2218/002
  USPC ...... 606/39, 41, 45, 48, 50; 607/98, 99, 101, 607/104, 105, 113, 115, 116
  See application file for complete search history.

(56) References Cited

U.S. PATENT DOCUMENTS

| | | | |
|---|---|---|---|
| 5,441,499 | A | 8/1995 | Fritzsch |
| 6,048,340 | A * | 4/2000 | Miyagi .............. A61B 18/1492 606/41 |
| 6,066,137 | A | 5/2000 | Greep |
| 6,325,800 | B1 * | 12/2001 | Durgin ............... A61B 18/1492 606/41 |
| 6,464,699 | B1 | 10/2002 | Swanson |
| 7,731,714 | B2 | 6/2010 | Miyajima et al. |
| 8,048,073 | B2 * | 11/2011 | Nakamura ......... A61B 18/1492 606/41 |
| 8,663,221 | B2 * | 3/2014 | Okada ................ A61B 18/1492 606/45 |
| 8,945,123 | B2 * | 2/2015 | Suzuki ............... A61B 18/1492 606/113 |
| 9,387,034 | B2 * | 7/2016 | Okada ..................... A61B 18/14 |
| 2001/0049509 | A1 | 12/2001 | Sekine et al. |
| 2004/0172018 | A1 * | 9/2004 | Okada ................ A61B 18/1402 606/46 |
| 2004/0210284 | A1 * | 10/2004 | Okada ................ A61B 18/1402 607/96 |
| 2005/0273097 | A1 | 12/2005 | Ryan |
| 2006/0276784 | A1 | 12/2006 | Miyajima et al. |
| 2011/0137123 | A1 * | 6/2011 | Suzuki ............... A61B 18/1477 600/127 |
| 2015/0088123 | A1 | 3/2015 | Sekino et al. |
| 2016/0008063 | A1 * | 1/2016 | Wake ................. A61B 17/3203 606/49 |
| 2017/0112361 | A1 | 4/2017 | Surti et al. |
| 2021/0113260 | A1 | 4/2021 | Tang et al. |

FOREIGN PATENT DOCUMENTS

| | | | |
|---|---|---|---|
| CN | 102379739 | A | 3/2012 |
| CN | 203183027 | U | 9/2013 |
| CN | 203861344 | U | 10/2014 |
| CN | 104507406 | A | 4/2015 |
| CN | 204364115 | U | 6/2015 |
| CN | 105434038 | A | 3/2016 |
| CN | 205359621 | U | 7/2016 |
| CN | 106214247 | A | 12/2016 |
| CN | 206324846 | U | 7/2017 |
| CN | 108272503 | A | 7/2018 |
| CN | 208808644 | U | 5/2019 |
| EP | 3761894 | B1 | 4/2022 |
| JP | H11114060 | A | 4/1990 |
| JP | 2004167081 | A | 6/2004 |
| JP | 2004313537 | A | 11/2004 |
| JP | 2006326157 | A | 12/2006 |
| JP | 2009233193 | A | 10/2009 |
| JP | 2009233269 | A | 10/2009 |
| JP | 2010119760 | A | 6/2010 |
| JP | 2015534884 | A | 12/2015 |
| KR | 10-20050033471 | A | 4/2005 |
| KR | 10-20070019599 | A | 2/2007 |
| KR | 10-20160141684 | A | 12/2016 |
| WO | 0172231 | A2 | 10/2001 |
| WO | 2015053365 | A1 | 4/2015 |
| WO | 2019169843 | A1 | 9/2019 |

OTHER PUBLICATIONS

Written Opinion of the International Searching Authority dated Nov. 13, 2018, for corresponding International Patent Application No. PCT/CN2018/104476, filed Sep. 7, 2018.
Search Report dated Nov. 13, 2018, for corresponding CN Priority Patent Application No. CN2018/101845766, filed Mar. 7, 2018.
Hearing Notice dated Sep. 11, 2023, for corresponding IN Patent Application No. 202027037306, filed Sep. 7, 2018.
Search Report dated Mar. 31, 2021, for corresponding EP Patent Application No. 18908663, filed Sep. 7, 2018.
Decision to Grant Patent dated Apr. 4, 2023, for corresponding CA Patent Application No. 3090198, filed Sep. 7, 2018.
Decision to Grant Patent dated Feb. 1, 2022, for corresponding EP Patent Application No. 18908663, filed Sep. 7, 2018.
Decision to Grant Patent dated Dec. 26, 2023, for corresponding IN Patent Application No. 202027037306, filed Sep. 7, 2018.
Decision to Grant Patent dated Apr. 14, 2022 for corresponding JP Patent Application No. 2020-543041, filed Sep. 7, 2018.
Decision to Grant Patent dated Aug. 18, 2022, for corresponding KR Patent Application No. 10-2020-7023347, filed Sep. 7, 2018.
Notice of acceptance for patent application dated May 4, 2021, for corresponding AU Patent Application No. 2018411482, filed Sep. 7, 2018.
Office Action dated Dec. 1, 2020, for corresponding AU Patent Application No. 2018411482, filed Sep. 7, 2018.
First Office Action dated Aug. 31, 2021, for corresponding CA Patent Application No. 3090198, filed Sep. 7, 2018.
Office Action dated May 25, 2021, for corresponding EP Patent Application No. 18908663, filed Sep. 7, 2018.
Office Action dated Aug. 9, 2021, for corresponding IN Patent Application No. 202027037306, filed Sep. 7, 2018.
Office Action dated Aug. 30, 2021, for corresponding JP Patent Application No. 2020-543041, filed Sep. 7, 2018.
Office Action dated Feb. 24, 2022, for corresponding KR Patent Application No. 10-2020-7023347, filed Sep. 7, 2018.
Office Action dated Nov. 20, 2023, for corresponding CN Priority Patent Application No. CN2018/10184576.6, filed Mar. 7, 2018.
Second Office Action dated Jun. 2, 2022, for corresponding CA Patent Application No. 3090198, filed Sep. 7, 2018.

* cited by examiner

DUAL-CHANNEL INJECTION BIPOLAR HIGH FREQUENCY ELECTROSURGICAL KNIFE

The present application is a national stage application of International application PCT/CN2018/104476 filed on Sep. 7, 2018 and entitled "Dual-Channel Injection Bipolar High Frequency Electrosurgical Knife," which International application claims the priority of the Chinese patent application No. 2018101845766 filed on Mar. 7, 2018 and entitled "Dual-Channel Injection Bipolar High Frequency Electrosurgical Knife," the contents of which are incorporated herein by reference as a part of the application.

BACKGROUND OF THE INVENTION

Technical Field

The invention relates to a medical bipolar high frequency electrosurgical knife in the field of medical instruments. In particular, the dual-channel injection bipolar high frequency electrosurgical knife integrates a cutting, marking, injecting and flushing function which can be used for an endoscope.

Description of Related Art

Over 50 years after endoscopic technology birth, it has gone through the stages of disease diagnosis to treatment. For the treatment of some digestive diseases has been very effective and reliable, and even has become the first choice for treatment. In recent years, with the development of endoscopic technology, endoscopic biopsy, endoscopic mucosal resection (EMR), and endoscopic submucosal dissection (ESD) has been widely used. The above methods are gradually becoming the preferred treatment for gastrointestinal bleeding, polypectomy, and early cancer, especially ESD plays a key role in the detection, diagnosis and resection of early cancer.

ESD is an endoscopic minimally invasive technique that uses high-frequency instruments to perform submucosal dissection of lesions (larger than 2 cm). Compared with traditional surgical procedures, ESD better retains the physiological functions of the digestive tract on the basis of cure tumors, and significantly improves the quality of life of patients after surgery. ESD has become the first choice for early cancer and precancerous lesions of the gastrointestinal tract including the esophagus.

However, the ESD procedure is complicated and usually takes a long time, and requires surgery under the guidance of an endoscope. First, the endoscope inserts into the human body to find the diseased tissue, and the device inserts into the human body through the endoscopic channel to lesion marking. After mark lesion and withdraw the device, use the injection needle for submucosal layer injection. Next, doctor performs surgery with a suitable electrosurgical knife, it will takes 1 to 2 hours to remove an early cancer lesion (approximately 3 cm) successfully, and make a specimens to pathological analysis. The instruments need to be changed during surgery, which make the surgery more cumbersome and prolong the operation time, causing pain to the patient. Therefore, it is necessary to develop a bipolar high frequency electrosurgical knife that integrates marking, cutting, injecting, and flushing functions.

BRIEF SUMMARY OF THE INVENTION

A dual-channel injection bipolar high frequency electrosurgical knife, which comprises an electrode part, a main part and an operation part.

Hereinafter, the electrode part is defined as distal end, and the operating part as proximal end. A dual-channel injection bipolar high frequency electrosurgical knife, which comprises an electrode part, a main part and an operation part. The electrode part is provided at the distal end of the dual-channel injection bipolar high frequency electrosurgical knife, comprising an active electrode for cutting tissue and injecting liquid. The active electrode can be extended or retracted relative to the distal end of the main part. The active electrode has a hollow tubular portion extended in the axial direction and a protrusion provided at the distal end thereof or only has a hollow tubular portion extending in the axial direction. The insulating part covers the outer surface of the active electrode for isolating the active electrode from the inert electrode, and the insulating part including a hollow tube and protruding structure at least on one side. The hollow tube is larger than the outer diameter of the hollow tubular portion of active electrode that allows liquid to flow between the active electrode and the insulating part. The inert electrode comprises a hollow tubular structure and a barb structure arranged at the distal end thereof. The barb structure can be engaged with the protruding structure of the insulating part. The main part is provided at the proximal end of the electrode part, including the insulation sheath. The insulation sheath comprises the first channel and the second channel. The first channel restrains the hollow tubular portion of the active electrode. The proximal end of hollow tubular portion of the active electrode connects with the insulation coated screw by the connector, thereby providing the first liquid passageway. The seal covers the outer surface of the connector and the insulation coated screw. The lumen size formed is smaller than the first channel, thereby forming a second liquid passageway in the first channel. The second channel can restrains a wire that can pass through the insulation sheath which constituting the second channel, and connected to the inert electrode which is covering the distal outer surface of the insulation sheath. The operation part is arranged at the proximal end of the main part, including the connection cable which is connected with the active electrode through the insulation coated screw and the inert electrode through the wire, and liquid inlets that can make the liquid separately flow to the first liquid passageway and the second liquid passageway.

The electrode part includes an active electrode, an insulating part and an inert electrode. The active electrode is provided at the distal end of the inert electrode, comprising a hollow tubular portion extending in the axial direction and a protrusion provided at the distal end thereof. The length extending from the vertical axis of the hollow tubular portion at the distal end of the active electrode is greater than the cross-section radius of the hollow tubular portion of the active electrode. The outwardly extending portion forms a protrusion at the distal end of the active electrode. Preferably, the cross-section of the protrusions is a divergent distribution, such as circumferential distribution, triangular distribution, and Y-shaped distribution. The protrusions can be hemisphere, sphere, cylinder, triangular prism, or Y-shaped. Depending on the specific surgical situation conditions and requests, doctors can choose different protrusions for cutting. The active electrode may also only have a hollow tubular portion extending in the axial direction. The active electrode is composed of metal material, which is not limited to a conductive material such as stainless steel, titanium, and tungsten. The active electrode can be extended or retracted, and cut the target lesion when extended.

The insulating part passes through the hollow tubular structure of the inert electrode and locates between the active electrode and the inert electrode for preventing conduction between the two electrodes. The insulating part is installed between the active electrode and the inert electrode. The active electrode passes through the hollow tube of the insulating part and can move relatively along the axial direction of the insulating part. The distal end of the inert electrode is provided with barb structure, and at least one side of the insulating part is provided with protruding structure, so that the insulating part and the inert electrode are interlocked and axially fixed. The material of the insulating material is metal oxide. The material is not limited to zirconia and other materials which have heat resistance and insulation, and the outer surface may be covered with a material such as polytetrafluoroethylene and other heat resistant and insulating materials. The hollow tube of the insulating part may be hollow cylinder, hollow triangular prism or hollow cylinder with a number of radial ends that are radiating outward along the center and at a certain angle to each other. An insulating part is installed between the inert electrode and the active electrode to prevent conduction between the two electrode. The active electrode, insulating part and inert electrode surface are covered with anti-blocking coating. The anti-blocking coating is not limited to titanium nitride (TiN), chromium nitride (CrN), aluminum titanium nitride (TiAlCN), titanium aluminum nitride (TiAlN), diamond-like carbon (DLC), polytetrafluoroethylene (PTFE).

When the active electrode is extended to the distal end and the distal surface of the seal comes into contact with the proximal surface of the insulating part, since the size of the tube formed by the seal is larger than the hollow tube size of the insulating part, the active electrode cannot continue to extend to the distal end, thereby acting as a restriction function, when the active electrode is retracted to the proximal end, the protrusion of the active electrode touch the insulating part, since the size of the protrusion is larger than the hollow tube size of the insulating part, the active electrode cannot continue to be retracted to the proximal end, thereby acting as a restriction function.

The main part is provided at the proximal end of the electrode part, comprising a protective tube, an insulation sheath, insulation coated screw, connector, seal and so on. The insulation coated screw including the conductive screw and the insulating coating on the surface. The conductive screw has elasticity and torque, which makes the insulation coated screw flexible. It not only provides liquid passageway for the product, but also allows it to flex freely in the endoscope. In addition, the resistance value of the insulation coated screw is smaller, and the larger current passed, so there is a better cutting effect.

The active electrode is connected with an insulation coated screw through a connector. The outer surface of the connector has a concave-convex structure, and the single-sided concave-convex structure is adopted. The proximal end of the connector is connected with an insulation coated screw. The seal is covered on the concave-convex structure side of the connector and the insulation coated screw by heat shrink, welding, adhesive bonding and so on. The concavo-convex structure allows the seal to cover the surface better for better sealing, which makes the electrosurgical knife to withstand 30 atm pressure. The side of the connector without concavo-convex structure connects to the hollow tubular portion of the active electrode.

The insulation sheath adopts double-channel structure, including the first channel and the second channel. The insulation sheath has outer insulation sheath and inner insulation sheath. At least one outer insulation sheath and inner insulation sheath are connected at their distal ends to form a sealed distal second channel. The first channel provided the active electrode pushed by insulation coated screw freely, make the active electrode extend out and retract into the insulation sheath smoothly and provide the first liquid passageway at the same time. The second channel can pass through the wire, and the distal end of the wire pass through the hole of the insulation sheath connects to an inert electrode which is covering the distal outer surface of the insulation sheath while the proximal wire connects to the connection cable. The inert electrode is fixed on the insulating sheath. The active electrode and the inert electrode are respectively connected to the operation part through an insulation coated screw and a wire. The insulation coated screw and wire are distributed in the two channels of the insulating sheath. There is an interstitial passageway between the insulating sheath and the seal. Liquid flows through the interstitial passageway to the proximal end of the insulating part, and then flows into the gap between the hollow tubular portion of the active electrode and the insulating part to form a second liquid passageway. If burnt tissue adheres to the cutting knife, there may be a spark or may not effectively cutting when power on. Connecting the second liquid passageway can clean the mucous tissues adhere on the active electrode and insulating part, and can also flush the hemorrhage site. The first liquid passageway and the second liquid passageway have a mutual positional of being in parallel, coaxial, or wound.

The operation part is arranged at the proximal end of the electrosurgical knife, including a positioning structure, a slider, a core rod, a connection sheath, an infusion tube and a connection cable. Among them, the slider is connected with the insulation coated screw to drive the active electrode. Inside of the slider has a connection sheath, connecting the insulation coated screw and the infusion tube. Both the positioning structure and the infusion tube have a liquid inlet, for example the 6% Luer taper. The infusion tube is connected with the insulation coated screw through the connection sheath to form the internal infusion passageway, and the positioning structure is connected with the insulating sheath to form the external infusion passageway. The normal saline, indicarmine and so on can be injected through the infusion pump in clinic.

The operating part is provided with a connection sheath. The distal end of the connection sheath is connected with the insulation coated screw, while the proximal end connected with the infusion tube. The proximal end of the infusion tube has a liquid inlet so that allow liquid to enter the first liquid passageway. The operating part is provided with a core rod and a slider moving back and forth along the core rod. Sliding slider can extend or retract the active electrode. The operating part is provided with a positioning structure. The positioning structure has a liquid inlet so that allow liquid to enter the second liquid passageway.

Preferably, the positioning structure is positioning cap, connecting to the core rod with a concave-convex structure.

Beneficial Effect:

The invention provides a dual-channel injection bipolar high frequency electrosurgical knife, the active electrode of the electrosurgical knife consists of the metallic material with hollow tubular portion, and form the first liquid passageway. Liquid can flow out from the hollow tubular portion of the active electrode, and inject solution in submucosal layer to elevate the mucosal tissue or clean the hemorrhage site.

There is an interstitial passageway between the insulating sheath and the seal of the present invention, and form a second liquid passageway. Liquid flows through the interstitial passageway to the proximal end of the insulating part and then flows into the gap between the hollow tubular portion of the active electrode and the insulating part, thereby clean the mucous tissue adhere on the active electrode and insulating part, and flush the hemorrhage site.

The main part of the present invention adopts the insulation coated screw, which not only provides liquid passageway for the product, but also allows it to flex freely in the endoscope.

The active electrode, insulating part and inert electrode surface of the present invention are covered with antiblocking coating to prevent tissue adhesion.

The distance between the active electrode and the inert electrode of the present invention is small, and the human tissue area which the high-frequency current flowing through is small, that can reduce the pain of surgery.

10. electrode part, 11. active electrode, 111. hollow tubular portion, 112. protrusion, 12. insulating part, 121. protruding structure, 13. inert electrode, 131. barb structure, 20. main part, 21. connector, 22. insulation coated screw, 23. seal, 24. protective tube, 25. insulation sheath, 26. wire, 251. outer insulation sheath, 252. inner insulation sheath, 27. first channel, 28. second channel, 29a. first liquid passageway, 29b. second liquid passageway, 30. operation part, 31. core rod, 32. connection sheath, 33. slider, 34. connection cable, 35. infusion tube, 36. positioning structure, 351. 6% Luer taper, 361. 6% Luer taper, 40. Lesion tissue, 50. hemorrhage site.

PREFERRED EMBODIMENTS

In order to make the purpose of the present invention, technical solutions and advantages clearer, an embodiment of the invention is described in detail with reference to the accompanying drawings.

It should be understood that the specific embodiments described herein are only used to explain the present invention and are not used to limit the present invention. The invention is not to be considered as being limited by the foregoing description, and is limited only by the scope of the appended claims. In order to provide a clearer description so that those skilled in the art can understand the contents of the application, the parts in the diagrams are not necessarily drawn according to their relative sizes. The proportions of certain dimensions and other relevant scales are highlighted and exaggerated. For simplicity of illustration, irrelevant or unimportant details are also not fully drawn.

Figure 1:
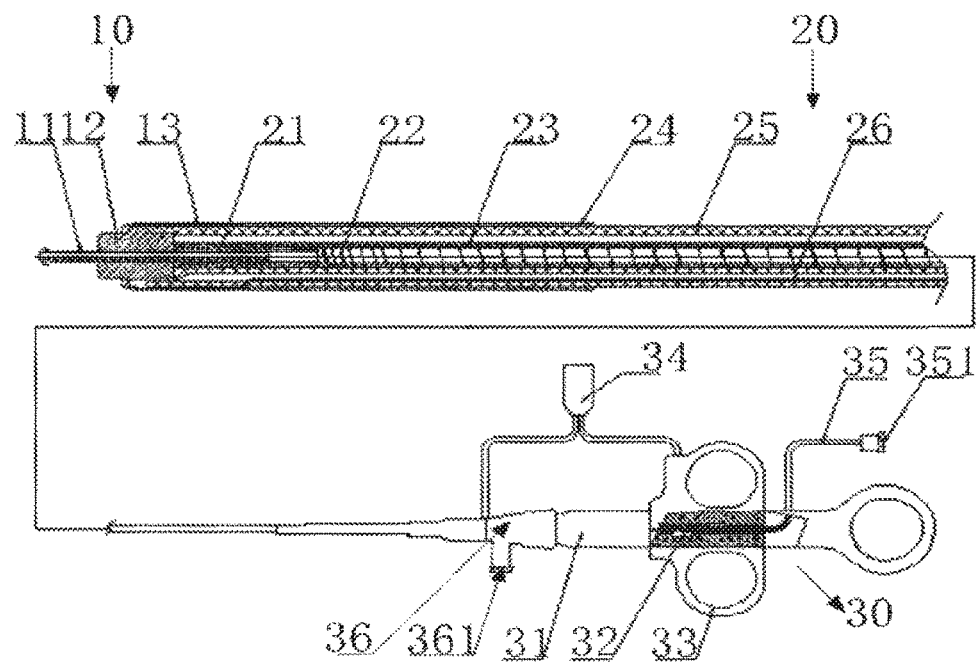
FIG. 1 is a schematic of the dual-channel injection bipolar high frequency electrosurgical knife.

As shown in FIG. 1, the dual-channel injection bipolar high frequency electrosurgical knife of the present invention comprises the electrode part 10, the main part 20, and the operation part 30. The electrode part 10 includes the active electrode 11, the insulating part 12, the inert electrode 13. The main part 20 includes the insulation sheath 25, the connector 21, the insulation coated screw 22, the seal 23, and the protective tube 24. The operation part 30 includes the core rod 31, the connection sheath 32, the slider 33, the connection cable 34, the infusion tube 35, and the positioning structure 36.

Hereinafter, the electrode part 10 is defined as a distal end, and the operation part 30 as a proximal end.

Figure 2:
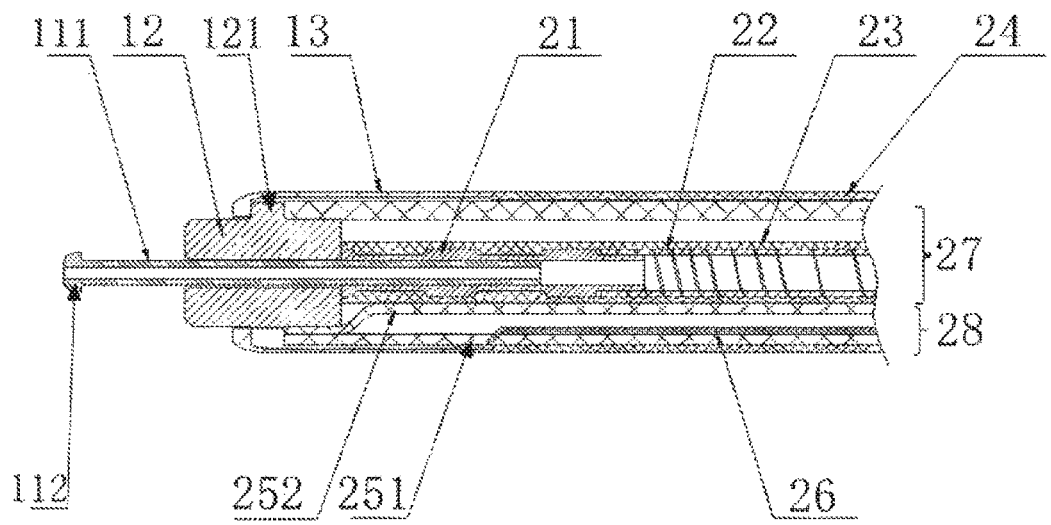
FIG. 2 is a partial enlarged schematic of the dual-channel injection bipolar high frequency electrosurgical knife.

As shown in FIGS. 1 and 2, the electrode part 10 is arranged at the distal end of the dual-channel injection bipolar high frequency electrosurgical knife. It can move axially along the main part 20, and the distal end of the electrode part 10 can extend and retract relative to the main part 20. The electrode part 10 includes the active electrode 11, the insulating part 12, the inert electrode 13.

Figure 5A:
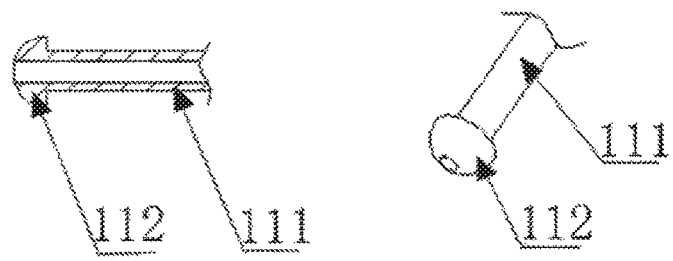
FIG. 5A-5F is a schematic of the distal end of the active electrode.
Figure 5B:
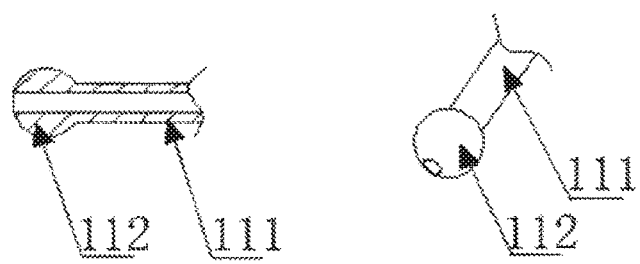
Figure 5C:
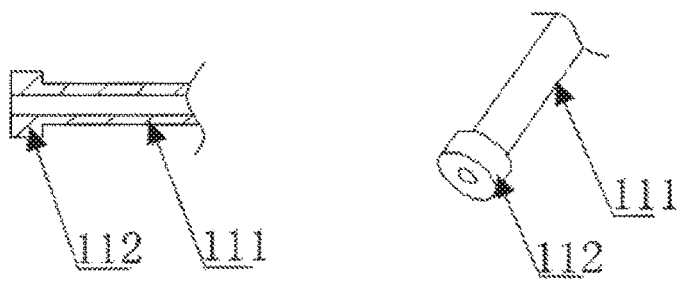
Figure 5D:
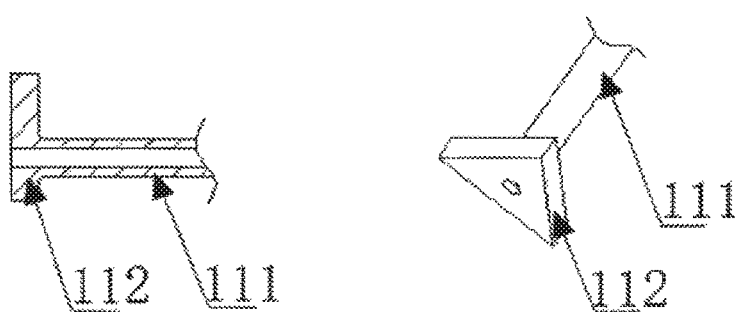
Figure 5E:
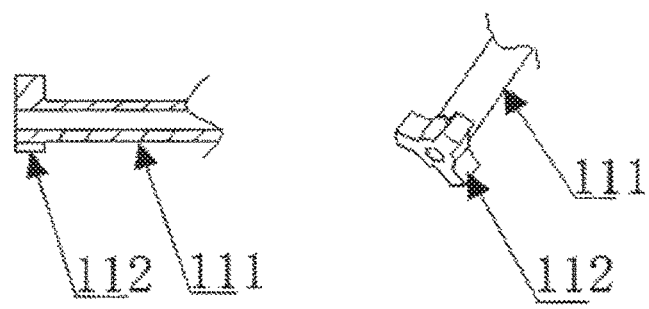
Figure 5F:
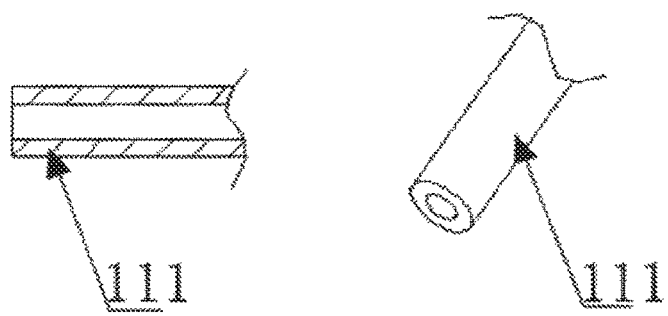

The active electrode 11 is used to cut tissue and inject liquid, and can be extended or retracted relative to the main part 20. The active electrode 11 is comprised of the hollow tubular portion 111 and the protrusion 112, and the distal end of hollow tubular portion 111 is provided with a protrusion 112. The hollow tubular portion 111 extends from the distal end to the proximal end of the bipolar high frequency electrosurgical knife, and is connected at the proximal end with the insulation coated screw 22. The protrusion 112 cross section of the active electrode 11 is divergent distribution. As shown in FIG. 5A, the cross-sectional profile of the protrusion 112 is circumferential distribution, and the protrusion 112 is a hemisphere. As shown in FIG. 5B, the cross section of the protrusion 112 is circumferential distribution and the protrusion 112 is a sphere. As shown in FIG. 5C, the cross section of the protrusion 112 is circumferential distribution, and the protrusion 112 is a cylinder. As shown in FIG. 5D, the cross section of the protrusion 112 is triangular distribution, and the protrusion 112 is a triangular prism. As shown in FIG. 5E, the cross section of the protrusion 112 is Y-shaped, and the protrusion 112 is Y-shaped. As shown in FIG. 5F, the active electrode 11 may also have only a hollow tubular portion 111 extending in the axial direction. The active electrode 11 may be a metal material such as stainless steel, titanium, tungsten, or the material which has conductivity.

Figure 6A:
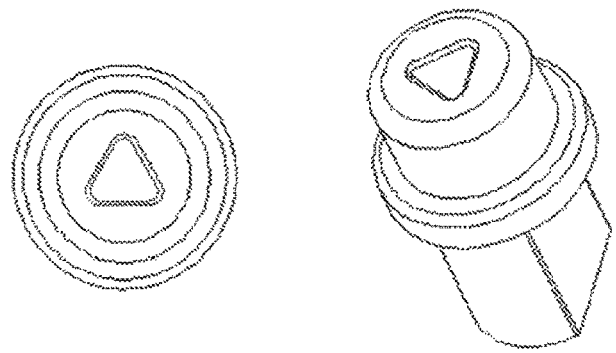
FIG. 6A-6C is a structure schematic of the insulating part.
Figure 6B:
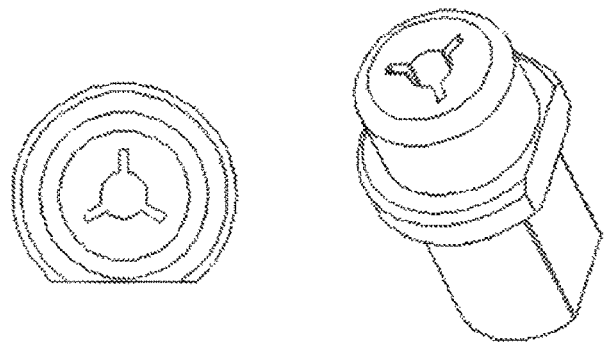
Figure 6C:
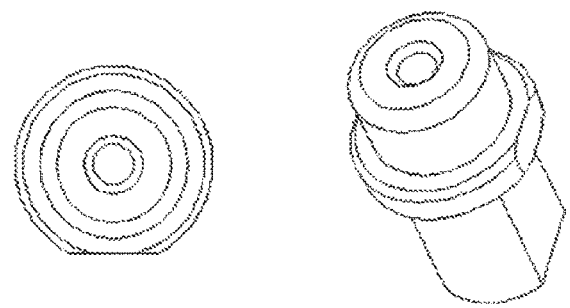

As shown in FIG. 2, the insulating part 12 is used for isolating the inert electrode 13 and the active electrode 11, ensuring that a current path can formed between the active electrode 11 and the inert electrode 13 when the two electrodes are in contact with the tissue at the same time. Moreover, the insulating part 12 can cooperate with the main part 20 to limit the extension of the active electrode 11. The insulating part 12 has a hollow tube, that covers the outer surface of the active electrode 11. The hollow tube size of the insulating part 12 is larger than the outer diameter of the hollow tubular portion 111 of the active electrode 11, allowing liquid to circulate between the two. As shown in FIG. 6A, the hollow tube of the insulating part 12 is a hollow triangular prism. As shown in FIG. 6B, the hollow tube of the insulating part 12 is a hollow cylinder with a number of radial ends that are radiating outward along the center and at a certain angle to each other. As shown in FIG. 6C, the hollow tube of the insulating part 12 is a hollow cylinder.

As shown in FIG. 2, the insulating part 12 is located between the active electrode 11 and the inert electrode 13. One side of the insulating part 12 is provided with a protruding structure 121, and the protruding structure 121 can be engaged with the inert electrode 13. The inert electrode 13 has a hollow tubular structure. The barb structure 131 is provided on the distal end of the inert electrode 13. The barb structure 131 can be engaged with the protruding structure 121 so that a stepped structure is formed between the inert electrode 13 and the insulating part 12. The proximal end of the inert electrode 13 covers the outer surface of the distal end of the insulation sheath 25 of the main part 20, and connects with the connection cable 34 through the wire 26 to achieve the conductive function of the inert electrode 13.

The active electrode 11, insulating part 12 and inert electrode 13 surface are covered with anti-blocking coating. The anti-blocking coating is not limited to titanium nitride (TiN), chromium nitride (CrN), aluminum titanium nitride (TiAlCN), titanium aluminum nitride (TiAlN), diamond-like carbon (DLC), polytetrafluoroethylene (PTNE).

Figure 7A:
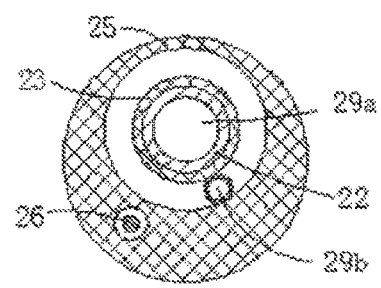
FIG. 7A-7C is a mutual position schematic of the first liquid passageway and the second liquid passageway.
Figure 7B:
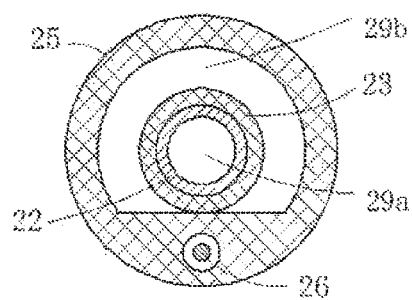
Figure 7C:
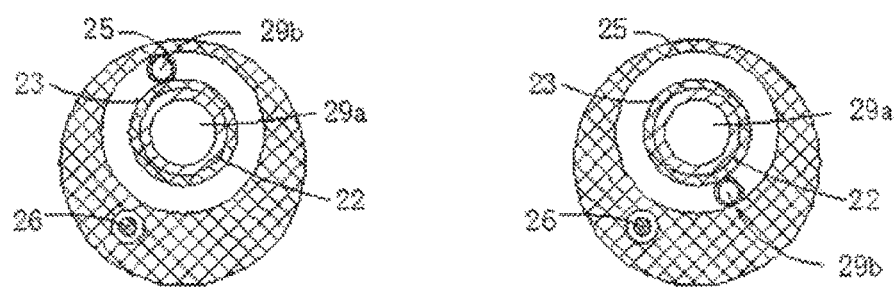

As shown in FIGS. 1 and 2, the main part 20 is provided at the proximal end of the electrode part 10, comprising the insulation sheath 25, connector 21, insulation coated screw 22, seal 23, and protective tube 24. The insulation sheath 25 adopts double-channel structure, including the outer insulation sheath 251 and the inner insulation sheath 252 that form the first channel 27 and the second channel 28. The first channel 27 can restrains the hollow tubular portion 111 of the active electrode 11, and the proximal end of the hollow tubular portion 111 connects to the insulation coated screw 22 through the connector 21, thereby providing the first liquid passageway 29a. There is an interstitial passageway between the insulation sheath 25 and the seal 23, forming the second liquid passageway 29b liquid flows through the interstitial passage to the proximal end of the insulating part 12, and then flows into the gap between the hollow tubular portion 111 of the active electrode 11 and the insulating part 12, so that can clean the active electrode 11 and the insulating part 12, and can also flush the hemorrhage site. The second channel 28 is a wire channel. The wire can pass through the outer insulation sheath 251 of the second channel 28 connect to the inert electrode 13 which is covering the distal end outer surface of the insulating sheath 25. As shown in FIG. 7A and FIG. 2, the first liquid passageway 29a and the second liquid passageway 29b are provided in the insulation sheath 25 as parallel position. As shown in FIG. 7B, the first liquid passageway 29a and the second liquid passageway 29b are provided in the insulation sheath 25 as coaxial position. As shown in FIG. 7C, the first liquid passageway 29a and the second liquid passageway 29b are provided in the insulation sheath 25 as winding position. The position of the second liquid passageway 29b in the cross section are different depending on the position of the cross section.

In the first channel 27, the proximal outer surface of the hollow tubular portion 111 of the active electrode 11 is provided with a connector 21, which have conductive function. The connector 21 adopts a hollow tubular structure and its outer surface can be a concave-convex structure. The proximal end of the connector 21 is connected to the insulation coated screw 22. The insulation coated screw 22 including the conductive screw and the insulating coating on the surface. The material of the insulating coating is polymer material. The proximal end of the insulation coated screw 22 is connected with the connection cable 34 and connected at the distal end with the connector 21 which having conductive function, thereby achieving the conductive function of the active electrode 11. The connector 21 is connected with the active electrode 11, and the hollow tubular portion 111 of the active electrode 11 connects with the insulation coated screw 22 through the connector 21, thereby providing the first liquid passageway 29a. The insulation coated screw 22 has elasticity and can provide torque, so that the bipolar high frequency electrosurgical knife can pass through the endoscope bend better.

The seal 23 is covered on the outer surface of the connector 21 and the insulation coated screw 22 by heat shrink, welding, adhesive bonding or other. The concavo-convex structure of the connector 21 allows the seal 23 to better cover the surface for better sealing, which makes the electrosurgical knife product to withstand 30 atm pressure. The size of the channel formed by the seal 23 is smaller than the first channel 27 ensuring that liquid can successfully pass through the second liquid passageway 29b, and the size of the channel formed by the seal 23 is larger than the hollow tube of the insulating part 12. Moreover, the distal outer surface of the insulation sheath 25 can also cover the protective tube 24. The proximal end of the inert electrode 13 covering the distal outer surface of the insulation sheath 25 may be connected to the distal end of the protective tube 24, and located together at the outest layer for electrical safety protection. The second channel 28 may be smaller, greater, or equal to the size of the first channel 27. Preferably, the size of the second channel 28 is smaller than the size of the first channel 27. The outer insulation sheath 251 and inner insulation sheath 252 are connected at their distal ends to form the second channel 28. The second channel 28 can restrains the wire 26 that can pass through the hole of the outer insulation sheath 251 and connect to the inert electrode 13 which is covering the distal outer surface of the insulation sheath 25. The wire 26 is connected to the connection cable 34 to achieve the conductive function of the inert electrode 13.

As shown in FIG. 1, the operation part 30 is arranged at the proximal end of the main part 20 so that the electrode part 10 can be extended or retracted relative to the distal end of the main part 20, and provide a channel for injecting liquid. The operation part 30 includes the core rod 31, the connection sheath 32, the slider 33, the connection cable 34, the infusion tube 35, 6% Luer taper 351, the positioning structure 36, and 6% Luer taper 361. The positioning structure 36 is used to connect the insulation sheath 25 and the core rod 31, and the wire 26 is connected with the connection cable 34. The positioning structure 36 has a 6% Luer taper 361, and can be used for injecting liquid. The slider 33 is provided with a connection sheath 32. The distal end of the connection sheath 32 is connected with the insulation coated screw 22 while the proximal end is connected with the infusion tube 35 which having a 6% Luer taper 351, and can be used for injecting liquid. The slider 33 can be moved back and forth along the core rod 31 to extend or retract the active electrode 11. The active electrode 11 is placed inside the target mucosal tissue during use. The infusion pump is connected to the 6% Luer taper 351, normal saline or indicarmine is used to inject into submucosal to elevate the mucosal tissue and form a liquid cushion so called "water cushion" under the mucous membrane. The "water cushion" forms an effective barrier between the muscular layer and the lesion and effectively prevents heat conduction, which makes the surgical view clearer. The blood vessels are squeezed and sealed by the "water cushion", and the risk of hemorrhage is significantly reduced. This liquid passageway can also clean the hemorrhage site. Moreover, there is no need to replace instruments frequently during the operation, which greatly reduces surgical time and improves surgical safety.

If burnt tissue adheres to the cutter knife during use, there may be a spark or no effective cutting when power on. The timely cleaning of the cutter knife can effectively prevent the occurrence of the above conditions. When mucosal tissue adhere to the active electrode 11, an infusion pump or a syringe may be connected to the 6% Luer taper 361 to inject liquid, such as normal saline. Liquid enters the second liquid passageway 29b through the 6% Luer taper and then flows through the gap between the hollow tubular portion 111 of the active electrode 11 and the insulating part 12, thereby reaches the active electrode 11 and clean the mucous tissue on the active electrode 11 and insulating part 12 at the same time. If there is tissue hemorrhage during electrode cutting, it can also use 6% Luer taper 361 injecting normal saline to clean the hemorrhage site.

As shown in FIGS. 1 and 2, when pushing the slider 33 to move distally along the core rod 31, the slider 33 pushes the active electrode 11 to protrude distally through the connection sheath 32. When the distal surface of the seal 23 touches the proximal surface of the insulating part 12, since the tube formed by the seal 23 is larger than the hollow tube of the insulating part 12, the active electrode 11 cannot continue to protrude distally, thereby acting as a restriction function. When pulling the slider 33 to move proximally along the core rod 31, the active electrode 11 is driven to recover proximally. When the protrusion 112 of the active electrode 11 touch the insulating part 12, since the size of the protrusion 112 is larger than the hollow tube of the insulating part 12, and stairs formed by differences in size limited the active electrode 11 to be pulled toward the proximal end, thereby acting as a restriction.

Figure 3A:
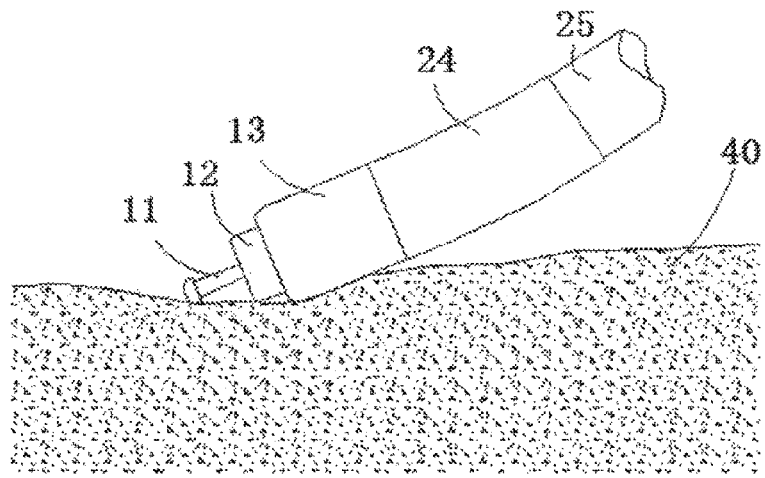
FIG. 3A-3B is a cutting schematic that the electrode part enters the lesion at different angles.

As shown in FIG. 3A, the outer surfaces of the active electrode 11 and the inert electrode 13 are against the lesion tissue 40 at the same time. The outer surfaces of the active electrode 11 and the inert electrode 13 are in close contact with the lesion 40 at present. Since the area of the active electrode 11 protrusion 112 is smaller than the inert electrode 13, the contact area between the active electrode 11 and the lesion tissue 40 is smaller than the inert electrode 13 and the lesion tissue 40. The resistance of the active electrode 11 in contact with the lesion tissue 40 is less than the inert electrode 13 and the lesion tissue 40. When in contact with the tissue, the current density at the active electrode 11 is greater than the inert electrode 13. The electrical energy is converted into heat energy, resulting in a higher surface temperature on the surface of active electrode 11, so that the active electrode 11 can cut the tissue.

Figure 3B:
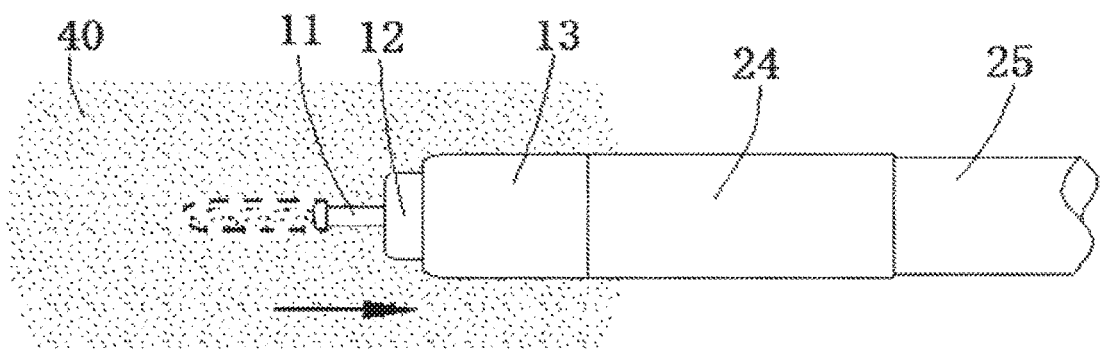

As shown in FIG. 3B, the lesion tissue 40 can be cut along the movement path of the active electrode 11 when the active electrode 11 and the inert electrode 13 at a high-frequency current on. At this time, the electrode part 10 enters the tissue to cut in a direction substantially perpendicular to the lesion tissue 40.

Figure 4A:
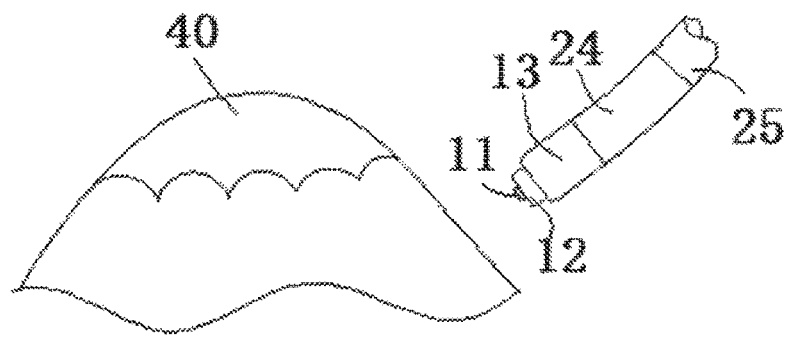
FIG. 4A-4G is a schematic illustrating the procedure of using the dual-channel injection bipolar high frequency electrosurgical knife.

FIG. 4A to 4G are used to describe the operation flow of the present invention, a dual-channel injection bipolar high frequency electrosurgical knife. As shown in FIG. 4A, dual-channel injection bipolar high frequency electrosurgical knife is inserted into the lesion tissue 40 through the value of the endoscope during surgery. In this process, the active electrode 11 is kept in a retracted state, and the protrusion 112 of the active electrode abuts against the insulating part 12, protecting the active electrode 11 and the endoscope not to be destroyed in the process.

Figure 4B:
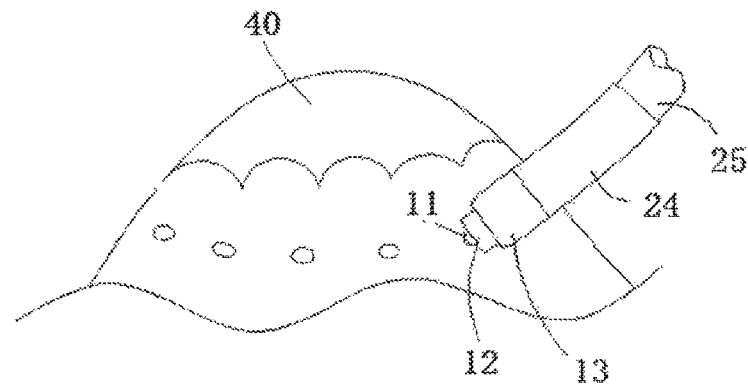

As shown in FIG. 4B, the active electrode 11 remains in the retracted state while the dual-channel injection bipolar high frequency electrosurgical knife reaches the lesion tissue 40, so that the active electrode 11 and the inert electrode 13 can in contact with the tissue at the same time. The connection cable 34 of the present invention is connected to an external high-frequency generator, wherein the high-frequency generator includes and not limits to 60-8200-230 (CONMED) 300D (ERBE), and VIO300S (ERBE). A high-frequency current is applied to the active electrode 11 and the inert electrode 13, and then marks around the lesion tissue 40. The high-frequency current is stopped after the marking is completed.

Figure 4C:
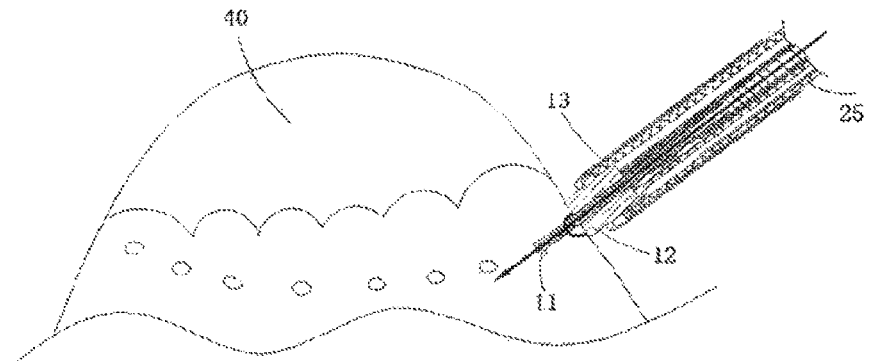
Figure 4D:
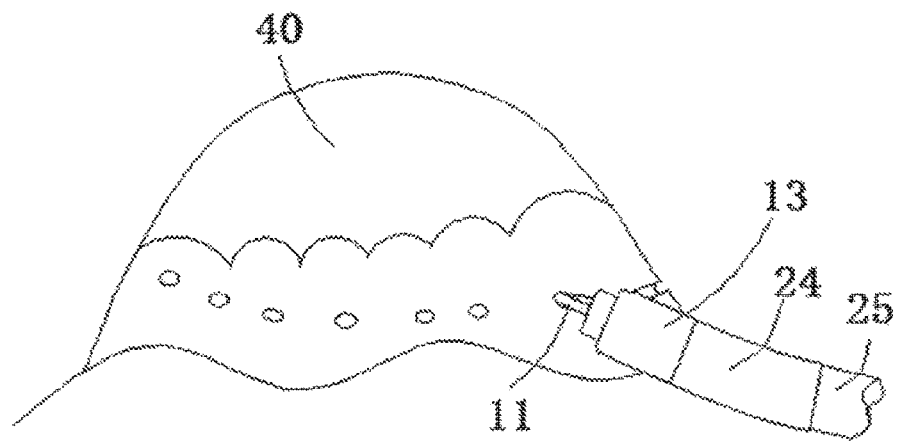

As shown in FIG. 4C to 4D, the slider 33 is pushed to extend the active electrode 11, place the active electrode 11 at the marked point and inserted into the submucosal of the lesion tissue 40. Then, inject the normal saline or indicarmine into the lesion tissue 40 through the 6% Luer taper 351 to elevate the mucosal tissue. After the lesion tissue is elevated, the active electrode 11 and the inert electrode 13 are kept in contact with the lesion tissue 40 at the same time, and then the active electrode 11 and the inert electrode 13 are supplied with a high-frequency current again so that the active electrode 11 can cut along the direction shown in FIG. 4D.

Figure 4E:
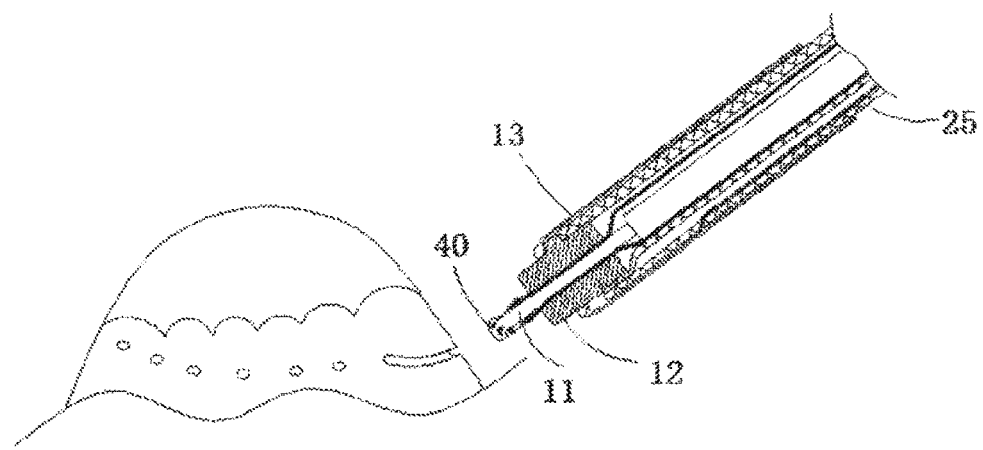

As shown in FIGS. 1 and 4E, the normal saline can flow through the 6% Luer taper 361 to clean the active electrode 11 or the insulating part 12 adhering with tissue during the cutting process.

Figure 4F:
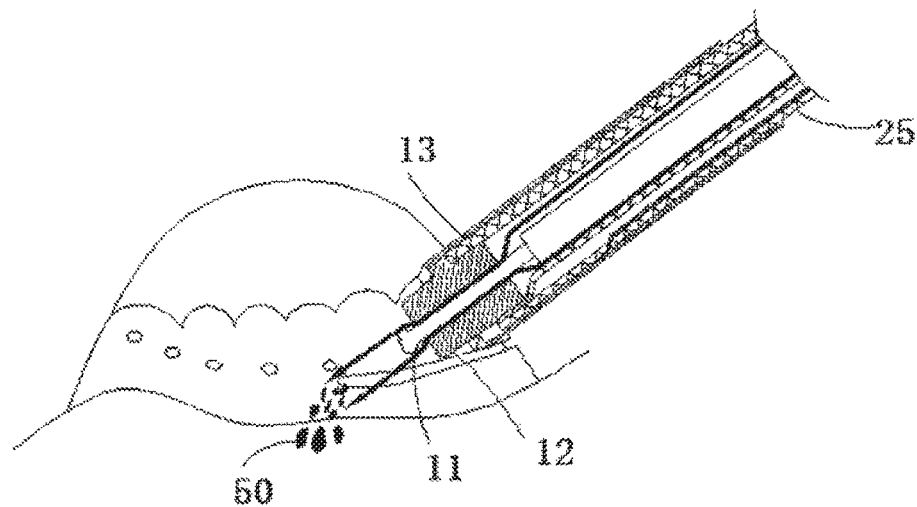

As shown in FIGS. 1 and 4F, if there is tissue hemorrhage during the cutting process, the hemorrhage site 50 can also be flushed with normal saline injected by the 6% Luer taper 361.

Figure 4G:
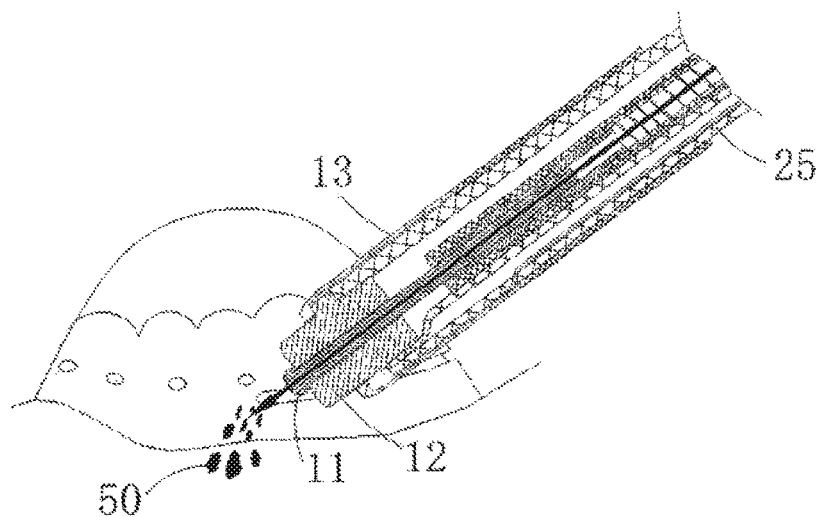

As shown in FIGS. 1 and 4G, if there is tissue hemorrhage during the cutting process, the hemorrhage site 50 can also be flushed with normal saline injected by the 6% Luer taper 351.

During the traditional operation, the surgeon marks the lesion with a needle knife first, then injects normal saline in the lesion with an injection needle to elevate the mucosal tissue, and cuts the lesion in the last. This method requires to replace the instruments frequently during the operation. The dual-channel injection bipolar high frequency electrosurgical knife of the present invention can realize the integrated functions of marking, liquid injecting, cutting, and cleaning without frequently replace instruments. It can achieve liquid injecting, flushing the hemorrhage site, and cleaning the cutting knifes, which greatly reduces surgical time and improves surgical safety.

Using the instrument constructed described above can achieve at least the following five functions. Firstly, the active electrode is adopted of metal material having a hollow tubular portion and protrusion so that form a first liquid passageway. Liquid can flow out from the hollow tubular portion of the active electrode, and inject into submucosal to elevate the mucosal tissue or clean the hemorrhage site. Secondly, there is an interstitial passageway between the outer insulating sheath and the seal, and form a second liquid passageway. Liquid flows through the second liquid passageway, thereby clean the adhered mucous tissue on the active electrode and insulating part, or flush the hemorrhage site. Thirdly, the insulation coated screw makes the main part has elasticity and torque, which allows it to flex freely and pass through the endoscope bend better. Fourthly, the active electrode, insulating part and inert electrode surface of the present invention are covered with anti-blocking coating to prevent tissue adhesion. Fifthly, the distance between the active electrode and the inert electrode of the present invention is small, and the human tissue area which the high-frequency current flowing through is small, that can reduce the pain of surgery.

The descriptions above are only the preferred embodiments of the present application, so that allow those skilled in the art understand or implement the invention of the present application. Various modifications and combinations of these embodiments are obvious to those skilled in the art. The general principles defined above can be implemented in other embodiments without departing from the concept of the present invention. Therefore, the present application will not be limited to these embodiments, but rather to the widest scope consistent with the principles and novel features disclosed herein.

What is claimed is:

1. A dual-channel injection bipolar high frequency electrosurgical knife comprising:
an electrode part, a main part and an operation part;
wherein the electrode part is provided at a distal end of the bipolar high frequency electrosurgical knife, comprising an active electrode configured for cutting tissue and injecting liquid, the active electrode is configured to be extendable or retractable relative to a distal end of the main part, the active electrode has a hollow tubular portion extending in an axial direction and a protrusion provided at a distal end thereof, an insulating part covers an outer surface of the active electrode for isolating the active electrode from an inert electrode, and the insulating part includes a hollow tube and a protruding structure at least on one side, the hollow tube is larger than an outer diameter of the hollow tubular portion of the active electrode that allows liquid to flow between the active electrode and the insulating part, the inert electrode comprises a hollow tubular structure and a barb structure arranged at a distal end of the inert electrode, and the barb structure is configured to be able to be engaged with the protruding structure of the insulating part;
the main part is provided at a proximal end of the electrode part, including an insulation sheath, the insulation sheath comprises a first channel and a second channel, the first channel restrains the hollow tubular portion of the active electrode, a proximal end of the hollow tubular portion of the active electrode connects with an insulation coated screw by a connector, thereby providing a first liquid passageway, a seal covers an outer surface of the connector and the insulation coated screw, wherein a size of the seal is smaller than the first channel, thereby forming a second liquid passageway in the first channel, the second channel restrains a wire that can pass through the insulation sheath constituting the second channel, and the wire is connected to the inert electrode, which covers a distal outer surface of the insulation sheath;
the operation part is provided at a proximal end of the main part, including a connection cable which is connected with the active electrode through the insulation coated screw and the inert electrode through the wire, and a first liquid inlet and a second liquid inlet configured to make the liquid separately flow to the first liquid passageway and the second liquid passageway.

2. The dual-channel injection bipolar high frequency electrosurgical knife according to claim 1, wherein the active electrode is arranged at the distal end of the inert electrode, and the protrusion extends outwardly from an axis of the hollow tubular portion of the distal end of the active electrode by a greater distance than a radius of a cross-section of the hollow tubular portion of the active electrode.

3. The dual-channel injection bipolar high frequency electrosurgical knife according to claim 2, wherein a cross section of the protrusion is a divergent distribution.

4. The dual-channel injection bipolar high frequency electrosurgical knife according to claim 1, wherein a cross section of the protrusion is a divergent distribution.

5. The dual-channel injection bipolar high frequency electrosurgical knife according to claim 1, wherein surfaces of the active electrode, insulating part and inert electrode are covered with anti-blocking coating.

6. The dual-channel injection bipolar high frequency electrosurgical knife according to claim 1, wherein the first liquid passageway and the second liquid passageway have a mutual position of being in parallel, coaxial, or wound.

7. The dual-channel injection bipolar high frequency electrosurgical knife according to claim 1, wherein the insulation coated screw includes a conductive screw and an insulating coating on a surface of the conductive screw, and the conductive screw has elasticity and torque.

8. The dual-channel injection bipolar high frequency electrosurgical knife according to claim 1, wherein a material of the insulating part is metal oxide.

9. The dual-channel injection bipolar high frequency electrosurgical knife according to claim 8, wherein the metal oxide is zirconia.

10. The dual-channel injection bipolar high frequency electrosurgical knife according to claim 1, wherein the insulation sheath has an outer insulation sheath and an inner insulation sheath.

11. The dual-channel injection bipolar high frequency electrosurgical knife according to claim 10, wherein the outer insulation sheath and the inner insulation sheath are connected to form the second channel which is sealed distally.

12. The dual-channel injection bipolar high frequency electrosurgical knife according to claim 10, wherein the seal is covered by heat shrink, welding and adhesive bonding.

13. The dual-channel injection bipolar high frequency electrosurgical knife according to claim 1, wherein the outer surface of the connector has concave-convex structure.

14. The dual-channel injection bipolar high frequency electrosurgical knife according to claim 1, wherein when the active electrode is extended to the distal end of the bipolar high frequency electrosurgical knife and a distal surface of the seal comes into contact with a proximal surface of the insulating part, since the size of the seal is larger than a size of the hollow tube of the insulating part, the active electrode cannot continue to extend distally, thereby acting as a first restriction function; when the active electrode is retracted proximally, the protrusion of the active electrode touches the insulating part, and since a size of the protrusion is larger than the size of the hollow tube of the insulating part, the active electrode cannot continue to be retracted proximally, thereby acting as a second restriction function.

15. The dual-channel injection bipolar high frequency electrosurgical knife according to claim 1, wherein the operation part is provided with a connection sheath, wherein a distal end of the connection sheath is connected with the insulation coated screw, while a proximal end of the connect sheath is connected with an infusion tube, and a proximal end of the infusion tube has the first liquid inlet that allows liquid to enter the first liquid passageway.

16. The dual-channel injection bipolar high frequency electrosurgical knife according to claim 1, wherein the operation part is provided with a core rod and a slider movable back and forth along the core rod, and the slider can extend or retract the active electrode.

17. The dual-channel injection bipolar high frequency electrosurgical knife according to claim 16, wherein the operation part is provided with a positioning structure, and the positioning structure has the second liquid inlet that allows liquid to enter the second liquid passageway.

18. A dual-channel injection bipolar high frequency electrosurgical knife comprising:
an electrode part, a main part and an operation part;
wherein the electrode part is provided at a distal end of the bipolar high frequency electrosurgical knife, comprising an active electrode configured for cutting tissue and injecting liquid, the active electrode is configured to be extendable or retractable relative to a distal end of the main part, and the active electrode has a hollow tubular portion extending in an axial direction, an insulating part covers an outer surface of the active electrode for isolating the active electrode from an inert electrode, the insulating part including a hollow tube and a protruding structure at least on one side, the hollow tube is larger than an outer diameter of the hollow tubular portion of the active electrode thereby allowing liquid to flow between the active electrode and the insulating part, the inert electrode comprises a hollow tubular structure and a barb structure arranged at a distal end of the inert electrode, and the barb structure is configured to be engaged with the protruding structure of the insulating part;
the main part is provided at a proximal end of the electrode part, including an insulation sheath, the insulation sheath comprises a first channel and a second channel, the first channel restrains the hollow tubular portion of the active electrode, a proximal end of the hollow tubular portion of the active electrode connects with an insulation coated screw by a connector, thereby providing a first liquid passageway, a seal covers an outer surface of the connector and the insulation coated screw, wherein a size of the seal is smaller than the first channel, thereby forming a second liquid passageway in the first channel, the second channel restrains a wire configured to be able to pass through the insulation sheath which constitutes the second channel, and the wire is connected to the inert electrode, which covers a distal end outer surface of the insulation sheath;
the operation part is arranged at a proximal end of the main part, including a connection cable which is connected with the active electrode through the insulation coated screw and which is connected with the inert electrode through the wire, and a first liquid inlet and a second liquid inlet-configured to make the liquid separately flow to the first liquid passageway and the second liquid passageway.

19. The dual-channel injection bipolar high frequency electrosurgical knife according to claim 18, wherein the active electrode, insulating part and inert electrode surface are covered with anti-blocking coating.

20. The dual-channel injection bipolar high frequency electrosurgical knife according to claim 18, wherein the insulation coated screw includes a conductive screw and an insulating coating on a surface of the conductive screw, and the conductive screw has elasticity and torque.

\* \* \* \* \*